US00PP25997P3

(12) United States Plant Patent
Lugli et al.

(10) Patent No.: US PP25,997 P3
(45) Date of Patent: Oct. 20, 2015

(54) CHERRY TREE NAMED 'PA3UNIBO'

(50) Latin Name: *Prunus avium*
Varietal Denomination: PA3UNIBO

(71) Applicant: Alma Mater Studiorum-Università degli Studi di Bologna, Bologna (IT)

(72) Inventors: Stefano Lugli, Modena (IT); Riccardo Correale, Bologna (IT); Michelangelo Grandi, Castenaso (IT)

(73) Assignee: Alma Mater Studiorum-Università degli Studi di Bologna, Bologna (IT)

( * ) Notice: Subject to any disclaimer, the term of this patent is extended or adjusted under 35 U.S.C. 154(b) by 118 days.

(21) Appl. No.: 13/986,703

(22) Filed: May 28, 2013

(65) Prior Publication Data

US 2013/0326773 P1 Dec. 5, 2013

(30) Foreign Application Priority Data

May 25, 2012 (QZ) ..... PBR 2012/1159

(51) Int. Cl.
*A01H 5/00* (2006.01)
*A01H 5/08* (2006.01)

(52) U.S. Cl.
USPC ..... Plt./181
CPC ..... *A01H 5/085* (2013.01)

(58) Field of Classification Search
USPC ..... Plt./181
See application file for complete search history.

*Primary Examiner* — Annette Para
(74) *Attorney, Agent, or Firm* — Hershkovitz & Associates, PLLC; Abraham Hershkovitz

(57) ABSTRACT

Variety Denomination 'PA3UNIBO' is a novel cherry tree of the genus/species (cultivar) *Prunus avium* derived from a seedling of unknown cross which was planted at Vignola, Modena Province, Italy. It was initially propagated by grafting to root stocks of varying vigor and, after testing in districts and plantings of differing types, proved to have the qualities proper to a promising new cultivar for the market.

5 Drawing Sheets

Latin name of the genus/species of the plant claimed (cultivar): *Prunus avium.*

Variety denomination: PA3UNIBO.

CROSS-REFERENCE TO RELATED APPLICATIONS

This application claims priority of pending EU Plant Patent for 'PA3UNIBO' which was filed on 25 May 2012 as Application No. 2012/1159 in the name of Applicant (holder) Alma Mater Studiorum—Università degli Studi di Bologna, the entire contents of which are expressly incorporated herein by reference. EU Trademark for 'Sweet Gabriel' was released on 2 Jan. 2013 as Registration No. 011051786 of Applicant (holder) Alma Mater Studiorum—Università degli Studi di Bologna. Such European Trademark is associated to PA3UNIBO and used to distinguish such cherry variety from the others.

FIELD OF THE INVENTION

*Prunus avium* 'PA3UNIBO' is derived from a seedling of unknown cross and originally called Selection DCA BO A1C40. It was planted at Vignola, Modena Province, Italy, in February 2002 and first cropped in 2004. It was initially propagated by grafting to root stocks of varying vigor, tested in different growing districts and planting densities and proved to have the properties proper to a promising new cultivar for the market. It picks in the beginning of June to the middle of June in Modena Province, about 14 days after 'Burlat', or a couple of days after 'Giorgia', and at about the same time as 'Summit', or about 4 days before 'Bing'.

SUMMARY OF THE INVENTION

The parentage of the variety is unknown. The names of varieties for comparison to comparable harvest dates are 'Giorgia' or 'Summit'. However, compared to 'Giorgia' and 'Summit', 'PA3UNIBO' has larger fruit (prevailing caliber of 30-32 mm) of firmer flesh, higher sugar content and more uniform ripening. The excellent stability of maturation guarantees a dialog collection of over 10 days. 'PA3UNIBO' was selected for its high qualities, including tree growth and yield performance, and fruit appearance and excellent taste-flavor properties, very sweet and with a good level of acidity. Its distinctive traits include mid-season picking, uniform maturing and large-sized fruit of firm flesh that is bright red (scale 4 CTIFL). The date of cross was in the year 2000. The location of the discovery was Vignola, Modena Province, Italy. The date of the first asexual propagation was in 2008 in Vignola, Modena Province, Italy. Variety Denomination 'PA4UNIBO' was originally propagated by grafting on 'Gisela 6' (U.S. Plant Pat. No. 8,954) root stock of differing vigor in trial fields of Bologna University to test growth and yield performance under medium-high density planting system.

BRIEF DESCRIPTION OF THE DRAWINGS

The accompanying photographs show typical specimens of the new variety as depicted in color as nearly true as is reasonably possible in color illustrations of this character.

DETAILED BOTANICAL DESCRIPTION OF THE VARIETY

Figure 1:
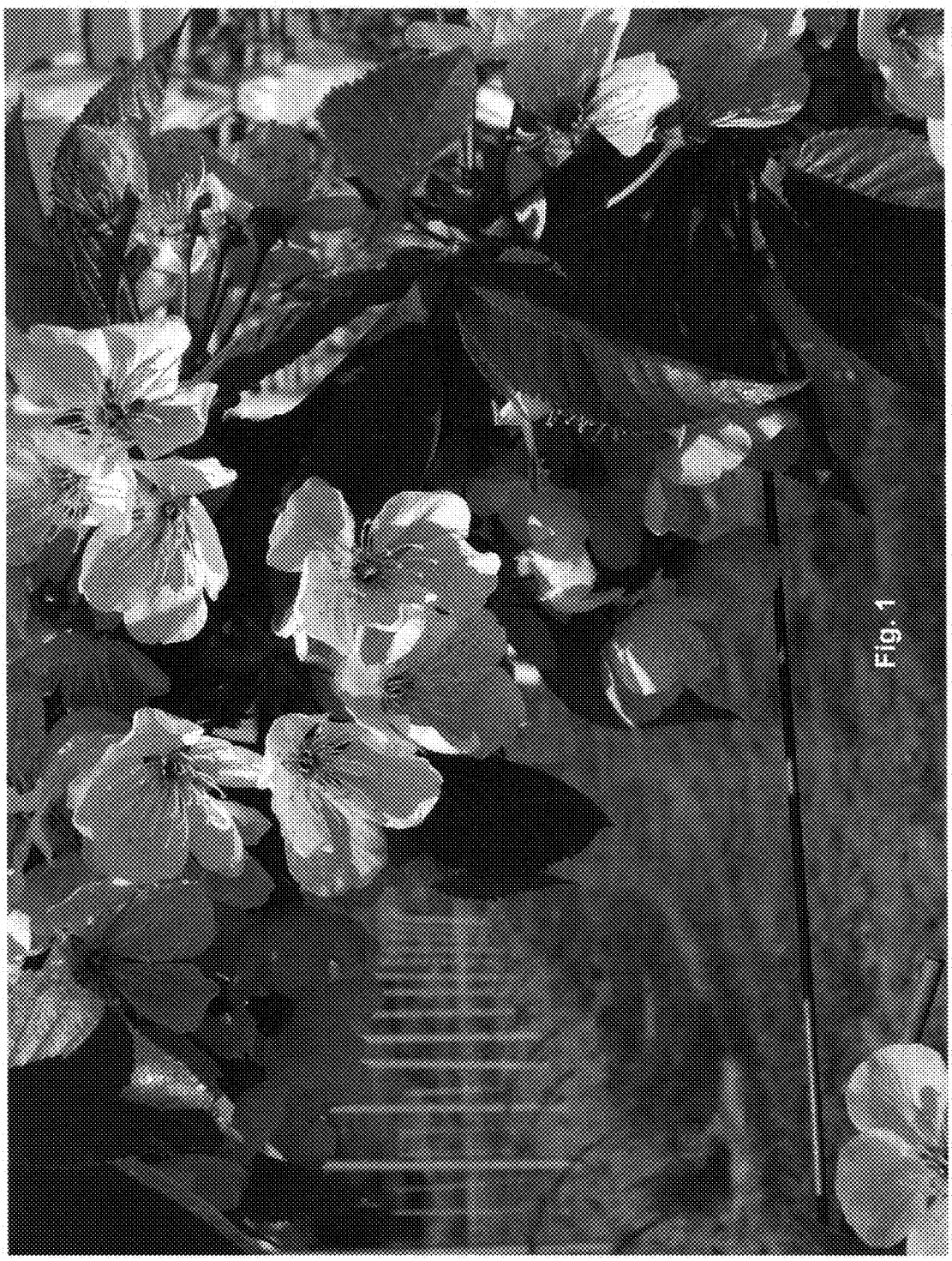
FIG. 1 illustrates the detail of fully-open blossoms of PA3UNIBO.
Figure 2:
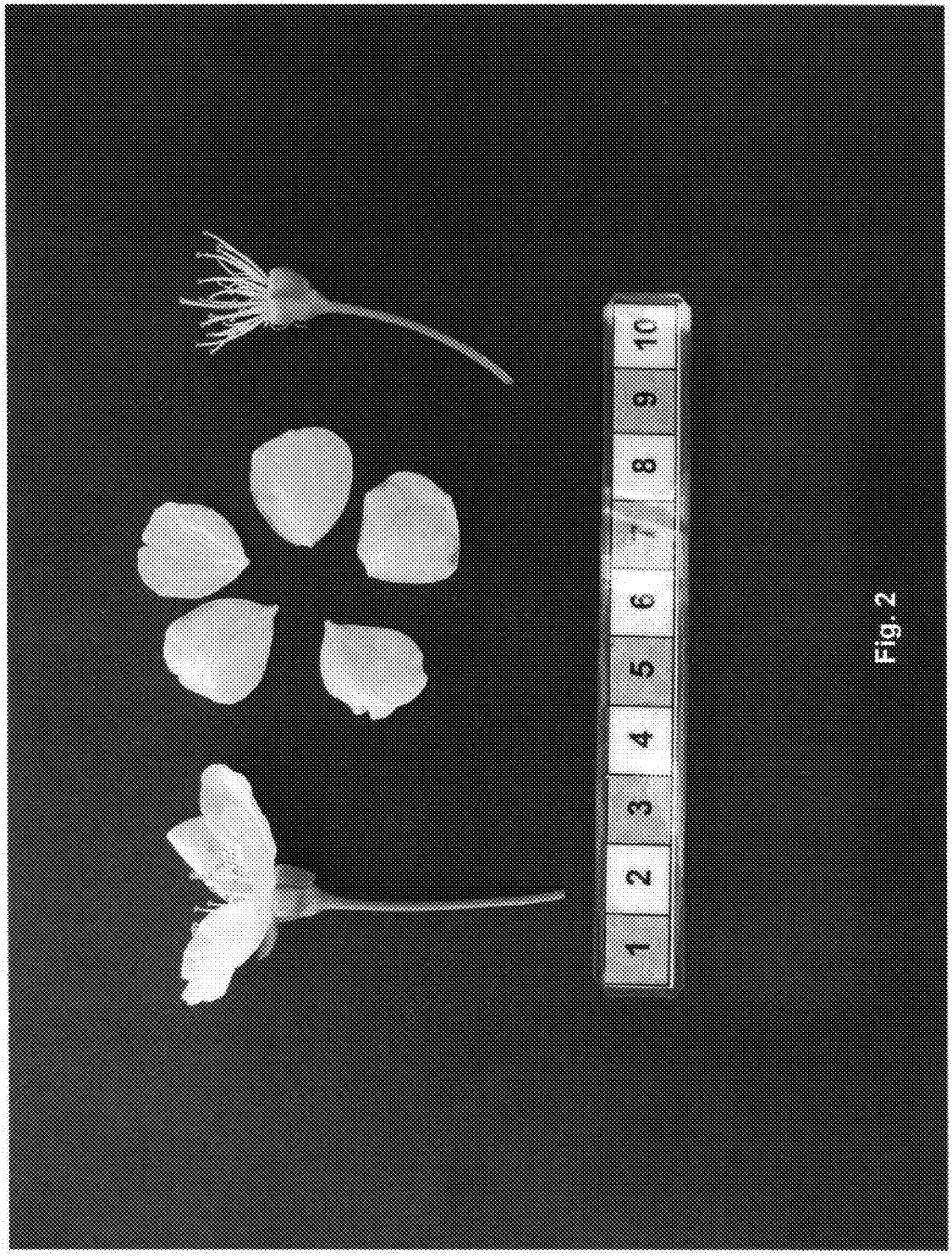
FIG. 2 shows the flower, full front, in profile and with separated petals, of PA3UNIBO.
Figure 3:
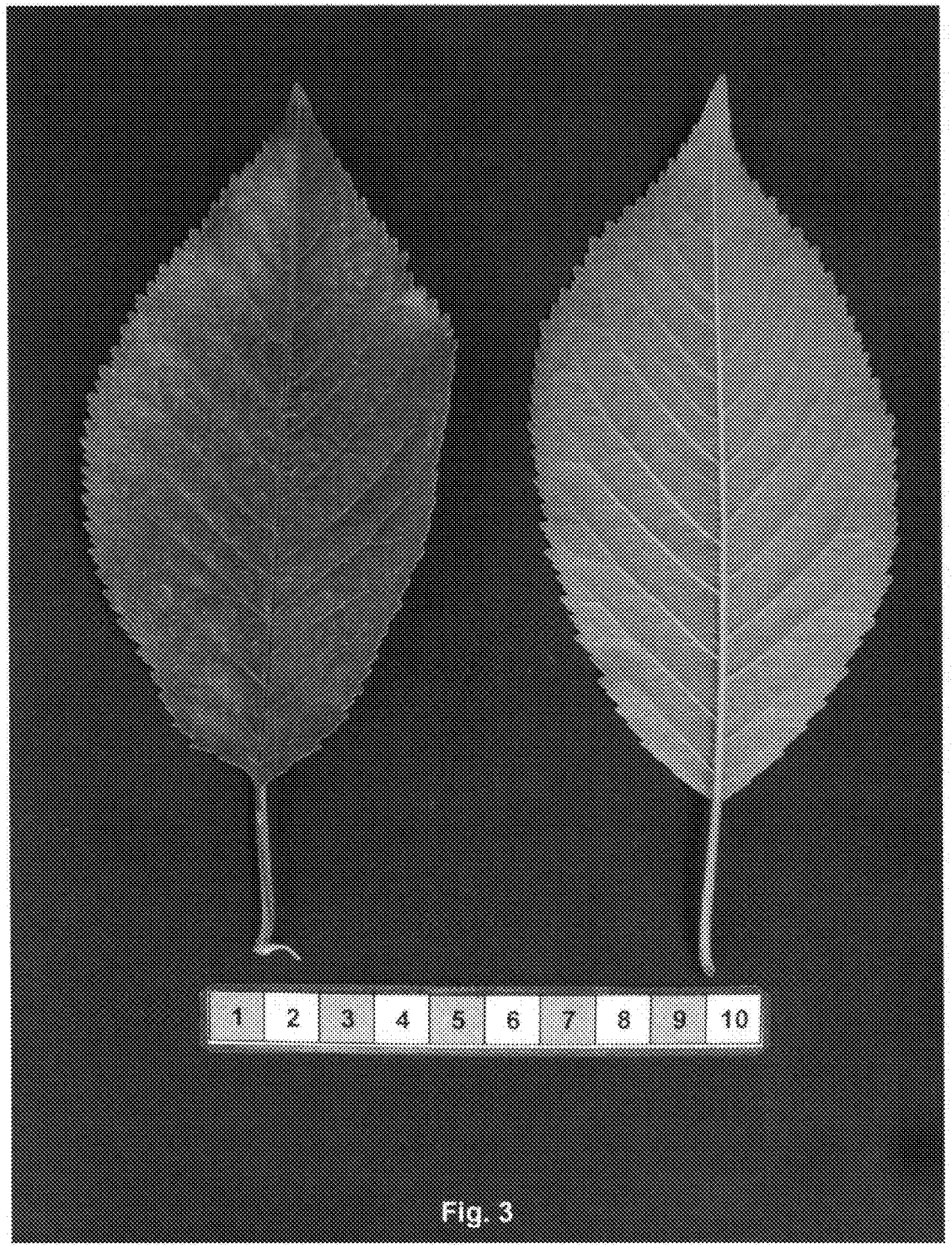
FIG. 3 shows the leaf profile of 'PA3UNIBO'. Two leaves have been detached and one has been placed upper leaf surface side down to show the lower leaf surface details.
Figure 4:
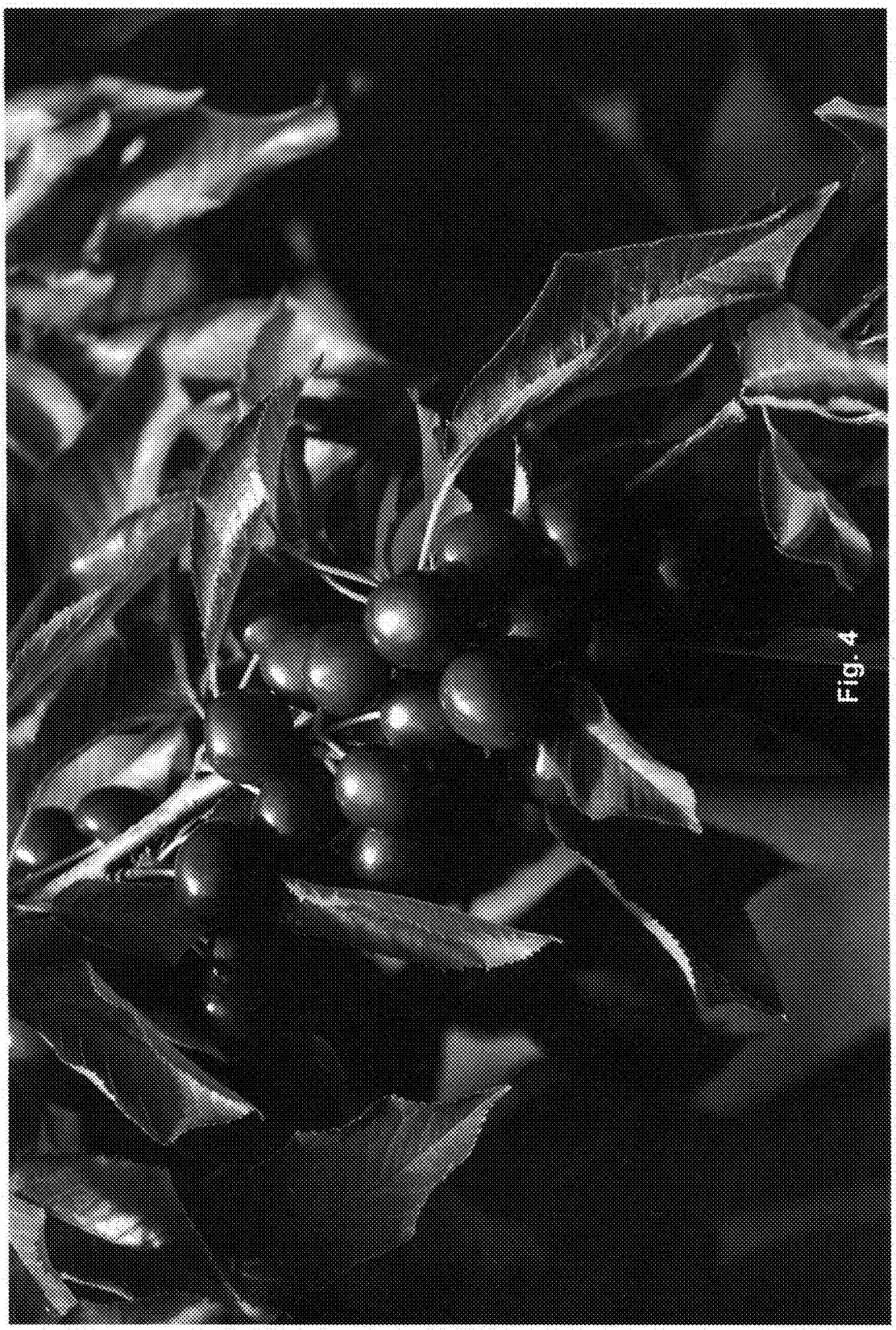
FIG. 4 shows details of fruit cropping of PA3UNIBO.
Figure 5:
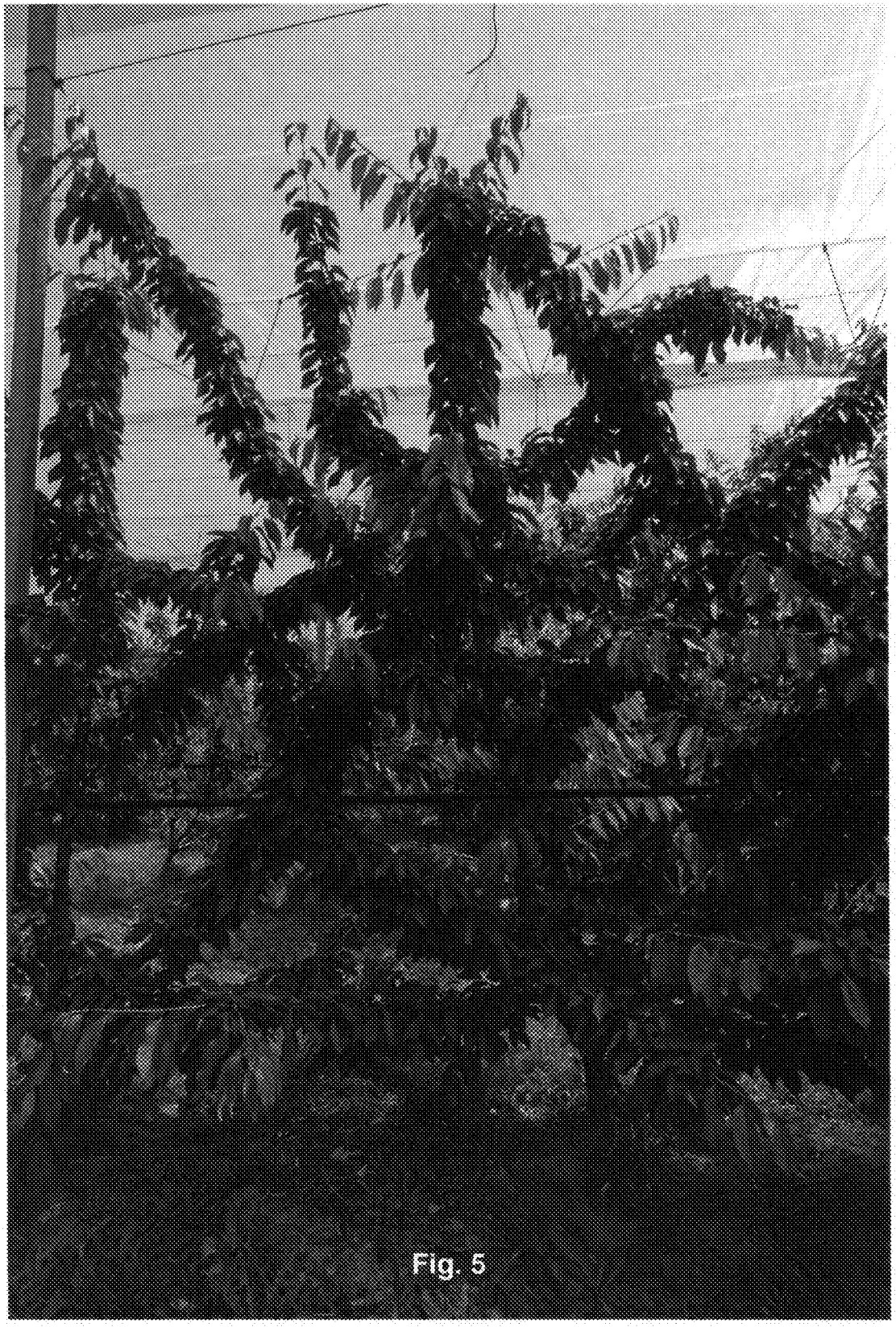
FIG. 5 shows the tree habit, with width-spread and height, of PA3UNIBO.

General:
- *Age of described tree(s).*—5 years, trained to palmette (hedge).
- *Location of described trees(s).*—Vignola, Modena Province, Italy.
- *Name of color chart used.*—Royal Horticultural Society Colour Chart.
- *Name of root stock.*—'Gisela 6'.

Tree:
- *Vigor.*—Medium-high.
- *Height.*—3.5-4 meters.
- *Spread.*—3 meters.
- *Growth habit.*—Open.
- *Canopy density.*—Medium.
- *Trunk diameter at specified height.*—15-17 cm diameter, as measured at about 5 cm above graft joint.
- *Trunk color.*—Grayish (201A) with reddish nuances (183A).
- *Bark texture.*—Of average roughness.
- *Tendency toward alternate bearing.*—No.
- *Winter hardiness.*—Unknown; no winter cold damage found in this Po Valley district.
- *Chilling requirement.*—Unknown.

Branch:
- *Length.*—300-320 cm of main branches.
- *Diameter.*—5-7 cm.
- *Crotch angle.*—About 45° depending on training system.
- *Bark color.*—Reddish-brown (200C) with some gray overtone (201A).
- *Bark texture.*—Fine, on average.

Current year shoot:
- *Length.*—40-60 cm.
- *Color.*—Reddish-brown (200C/200D) with some gray overtone (201A).

Winter hardiness:
- *USDA hardiness zone.*—Unknown.
- *Chilling requirement.*—Unknown.

Flower buds:
- *Number per spur.*—3-5, mostly 4.
- *Shape.*—Elliptical.
- *Length.*—1.3-1.4 cm.
- *Diameter.*—Under 1 cm.
- *Color.*—Reddish perules (187C).

Flowers:
- *Number per cluster.*—Minimum 8 to maximum 14 per spur; 2-3 per bud, mostly 3. Bloom is abundant.
- *Relative position of petals.*—Some flowers have slightly overlapping petal, others make contact only at margins.
- *Diameter.*—34-38 mm.
- *Depth.*—14-18 mm, measured as distance from receptacle to maximum petal aperture.
- *Is pollen produced?.*—Yes.
- *Coloration of pollen.*—Yellow (13A).

Sepal:
- *Length.*—5-7 mm.
- *Shape.*—Conical.
- *Width.*—4-5 mm.
- *Apex.*—Pointed.
- *Base.*—Pointed.
- *Margin descriptors.*—Regular margin.
- *Color—upper surface.*—Green (139C).
- *Color—lower surface.*—Pale green (138C).

Petals:
- *Number per flower.*—5.
- *Shape.*—Circular.
- *Length.*—16-19 mm.
- *Width.*—16-19 mm.
- *Apex.*—Slightly sunken.
- *Base.*—Slightly pointed.
- *Margin.*—Slightly undulated.
- *Color—upper surface.*—White (155B).
- *Color—lower surface.*—White (155B).

Bloom:
- *Date of bud burst.*—7-8 Apr. 2013.
- *Date of first bloom.*—13 Apr. 2013.
- *Date of full bloom.*—16 Apr. 2013.

Pedicel:
- *Length.*—31-35 mm.
- *Diameter.*—1-1.2 mm.
- *Color.*—Green (143B).

Pistil:
- *Quantity.*—1.
- *Size.*—21-23 mm.
- *Color.*—Green (143C).

Anthers:
- *Quantity.*—25-28; about 70% of 10-12 mm length, positioned slightly below the top of the stigma; in some flowers, 1-2 anthers are longer than the top of the stigma. The remaining 30% are 5-8 mm in length. White filament (155D).
- *Size.*—About 1 mm in diameter.
- *Color.*—Orange-yellow (15A).

Stigma:
- *Quantity.*—1.
- *Size.*—1-1.2 mm.
- *Color.*—Green (142A).

Styles:
- *Quantity.*—1.
- *Size.*—15-16 mm length.
- *Color.*—Pale-white green (142C) turning rosé (36C) towards end of bloom.

Ovary/ies:
- *Quantity.*—1.
- *Size.*—6-7 mm.
- *Color.*—Green (143C).

Leaves:
- *Length.*—12.3-12.8 cm.
- *Width.*—6.6-7.1 cm.
- *Shape.*—Elliptical.
- *Apex shape.*—Pointed.
- *Base shape.*—Pointed.
- *Margin.*—Fine toothed.
- *Color—upper surface.*—Dark green (137A).
- *Color—lower surface.*—Pale green (138A/138B) with central green-yellow veining (152A/152B).

Petiole:

*Length.*—3.1-3.7 cm.

*Diameter.*—Slightly less than 2 mm.

*Color.*—Green-yellow (152A/152B) under and reddish upper (183A).

Fruit:

*Shape.*—Heart-shaped.

*Diameter.*—30-32 mm.

*Height.*—25-28 mm.

*Weight.*—12-14 g, average weight.

*Number per cluster.*—7-11 per spur.

*Skin color* (*include ground color and over color*).—Bright red (185A) tending toward bright purplish-red (187B) at advanced maturity.

*Presence of lenticels.*—Yes.

*Density of lenticels.*—Medium.

*Skin thickness.*—Medium.

*Skin texture.*—Medium.

*Anthocyanin coloration present near skin?.*—No.

*Tenacity of flesh to stone.*—Low.

*Flesh color.*—Rosé (52A).

*Flesh texture.*—Fine.

*Juiciness.*—High.

*Juice analysis* (*brix, acidity, tss, etc.*).—17.4° Brix and 8.1 g/l malic acid (2012 data).

*Stone size.*—Medium.

*Stone shape.*—Elliptical.

*Stone color.*—Pale brown (165D).

Fruit stem:

*Length.*—33-36 mm.

*Diameter.*—Over 1 mm.

*Color.*—Green (143B).

Harvest:

*Maturity date range.*—June 1-June 20, about a couple of days after 'Giorgia' and just before 'Summit', approximately 14 days after 'Burlat' or 4 days before 'Bing'. Optimum harvest dates for 'PA3UNIBO' in Modena Province are June 5-June 10.

*Harvest date range* (*if different*).—Same as above.

The diploid cultivar 'PA3UNIBO' is not self-fertile (with the allelic profile of S1S4), and requires pollinators for optimum fruit load and yield. Pollinators include Sweet Aryana® ('PA1UNIBO'*) (U.S. Plant patent application Ser. No. 13/986,702), Sweet LORENZ® ('PA2UNIBO'*) (U.S. Plant patent application Ser. No. 13/986,701), Sweet Valina® ('PA4UNIBO'*) (U.S. Plant patent application Ser. No. 13/986,704) and Sweet Saretta® ('PA5UNIBO'*) (U.S. Plant patent application Ser. No. 13/986,686). Other same-species pollinators are anticipated to be compatible and prove productive.

Under observation during planting, growing and harvesting under normal cultural and growing conditions in Modena Province, Italy, no particular insect or plant/fruit disease resistance or susceptibility has been observed.

Because of the outstanding and unique horticultural characters of the claimed plant, especially its long harvest period and large size, this cherry can be planted to extend the cultivar's season. Although this new variety of cherry possesses the above-described characteristics, it is to be understood that variations and fluctuations may occur in the magnitude and qualities due to changes in growing and climate conditions, irrigation, fertilization, pruning and pest control.

What is claimed is:

1. A new and distinct cherry tree as herein described and illustrated.

* * * * *